United States Patent [19]

Schmitt et al.

[11] Patent Number: 5,728,867

[45] Date of Patent: Mar. 17, 1998

[54] CARBONYLOXY-SUBSTITUTED AZULENESQUARIC ACID DYES, INTERMEDIATES THEREFOR AND OPTICAL RECORDING MEDIUM

[75] Inventors: Michael Schmitt, Weinheim; Wolfgang Schrott, Lugwigshafen; Peter Neumann, Mannheim; Sibylle Brosius; Klaus Dieter Schomann, both of Ludwigshafen; Harald Kuppelmaier, Goennheim, all of Germany

[73] Assignee: BASF Aktiengesellschaft, Ludwigshafen, Germany

[21] Appl. No.: 603,025

[22] Filed: Oct. 25, 1990

[30] Foreign Application Priority Data

Oct. 25, 1989 [DE] Germany .......................... 39 35 524.1

[51] Int. Cl.[6] .................................................. C07C 69/52
[52] U.S. Cl. ........................... 560/221; 560/128; 560/103
[58] Field of Search ............................ 560/221, 128, 560/103

[56] References Cited

FOREIGN PATENT DOCUMENTS

| 0310080 | 4/1989 | European Pat. Off. . |
| 3505750 | 8/1986 | Germany . |
| 3505751 | 8/1986 | Germany . |

OTHER PUBLICATIONS

Angewandte Chemie, 78, 1966, p. 937, W. Ziegenbein, et al., "Kondensationsprodukte Aus Quadratsaure Und Azulen--Kohlenwasserstoffen".

Dyes and Pigments, vol. 8, 1987, pp. 381–388, S.H. Kim, et al., "Synthesis and Characteristics of Infrared Absorbing 2:1 Nickel Complex Dyes".

Journal of Organic Chemistry, Band 38, Nr. 6, 1973, Seiten 1106–11–American Chemical Society, Easton, US; R.N. McDonald et al.: "Nonbe aromatic systems" *Seite 1107, right–hand column, formulas; page right–hand column, formulas*.

*Primary Examiner*—Paul J. Killos
*Attorney, Agent, or Firm*—Oblon, Spivak, McClelland, Maier & Neustadt, P.C.

[57] ABSTRACT

Carbonyloxy-substituted azulenesquaric acid dyes of the formula

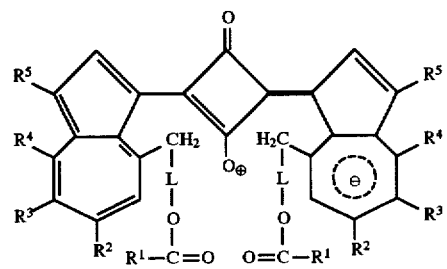

where

L is $C_1$–$C_{12}$-alkylene which may be substituted by phenyl, $R^1$ is $C_1$–$C_{12}$-alkyl, monounsaturated or polyunsaturated $C_3$–$C_{12}$-alkenyl, which may be phenyl-substituted, $C_3$–$C_7$-cycloalkyl, $C_3$–$C_7$-cycloalkenyl, substituted or unsubstituted phenyl, pyrrolyl, furanyl, thienyl or pyridyl and $R^2$, $R^3$, $R^4$ and $R^5$ are each independently of the others hydrogen or substituted or unsubstituted $C_1$–$C_{12}$-alkyl, with the proviso that when $R^3$ is hydrogen the positions of the substituents $CH_2$—L—O—CO—$R^1$ and $R^4$ on either or both azulene rings may also be interchanged with each other within an azulene ring, are useful in an optical recording medium.

4 Claims, No Drawings

CARBONYLOXY-SUBSTITUTED AZULENESQUARIC ACID DYES, INTERMEDIATES THEREFOR AND OPTICAL RECORDING MEDIUM

The present invention relates to novel carbonyloxy-substituted azulenesquaric acid dyes of the formula

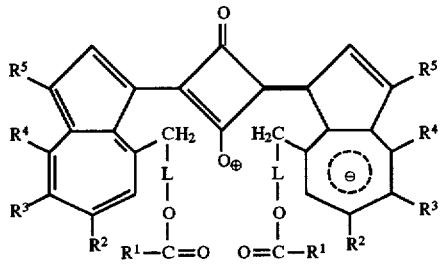

(I)

where

L is $C_1$–$C_{12}$-alkylene which may be substituted by phenyl, $R^1$ is $C_1$–$C_{12}$-alkyl, monounsaturated or polyunsaturated $C_2$–$C_{12}$-alkenyl, which may be phenyl-substituted, $C_3$–$C_7$-cycloalkyl, $C_3$–$C_7$-cycloalkenyl, substituted or unsubstituted phenyl, pyrrolyl, furanyl, thienyl or pyridyl and $R^2$, $R^3$, $R^4$ and $R^5$ are identical or different and each is independently of the others hydrogen or $C_1$–$C_{13}$-alkyl which may be substituted by halogen, $C_1$–$C_{12}$-alkoxy, phenyl, substituted phenyl, $C_1$–$C_{12}$-alkoxycarbonyl or by cyano, with the proviso that when $R^5$ is hydrogen the positions of the substituents $CH_2$—L—O—CO—$R^1$ and $R^4$ on either or both azulene rings may also be interchanged with each other within an azulene ring; to intermediates therefor; and to an optical recording medium which contains the novel dyes.

The cost-efficient manufacture of optical data recording media requires dyes having particular properties. These dyes should

- be strongly absorbing within the range from 700 to 900 nm to provide layers that may be writable with semiconductor lasers,
- in layer form be highly reflective in the near infrared (700–900 nm) to make possible a simple layer construction (without reflector layer),
- be highly soluble, for example in order that the thin storage layer may be applied to a base material by spincoating, and
- be highly stable in thin layers.

The prior art storage materials frequently are defective on at least one count.

It is an object of the present invention to provide novel dyes which are free or substantially free of the abovementioned defects.

We have found that this object is achieved by the carbonyloxy-substituted azulenesquaric acid dyes of the formula I defined at the beginning.

Any alkylene and alkyl appearing in the abovementioned formula I may be either straight-chain or branched.

In any substituted phenyl appearing in the formula I, suitable substituents are for example $C_1$–$C_4$-alkyl, $C_1$–$C_4$-alkoxy and halogen (preferably fluorine, chlorine or bromine).

L is for example methylene, ethylene, 1,2- or 1,3-propylene, 1,2-, 1,3-, 2,3- or 1,4-butylene, pentamethylene, hexamethylene, heptamethylene, octamethylene, nonamethylene, decamethylene, undecamethylene, dodecamethylene, phenylethylene or 1-phenyl-1,3-propylene.

$R^1$, $R^2$, $R^3$, $R^4$ and $R^5$ in the formula I are each for example methyl, ethyl, propyl, isopropyl, butyl, isobutyl, sec-butyl, tert-butyl, pentyl, isopentyl, neopentyl, tert-pentyl, hexyl, 2-methylpentyl, heptyl, octyl, 2-ethylhexyl, nonyl, decyl, undecyl or dodecyl.

$R^1$ may also be for example ethenyl, propenyl, butenyl, butadienyl, pentenyl, pentadienyl, hexenyl, hexadienyl, hexatrienyl, heptenyl, heptadienyl, heptatrienyl, ocetenyl, octadienyl, octatrienyl, octatetraenyl, nonenyl, nonadienyl, nonatrienyl, nonatetraenyl, decenyl, decadienyl, decatrienyl, decatetraenyl, decapentaenyl, undecenyl, undecadienyl, undecatrienyl, undecatetraenyl, undecapentaenyl, dodecenyl, dodecadienyl, dodecatrienyl, dodecatetraenyl, dodecapentaenyl, dodecahexaenyl, styryl, cyclopentyl, cyclopentenyl, cyclopentadienyl, cyclohexyl, cyclohexenyl, cyclohexadienyl, cycloheptyl, cyclopentenyl, chcloheptadienyl or cycloheptatrienyl.

$R^2$, $R^3$, $R^4$ and $R^5$ may each also be for example fluoromethyl, chloromethyl, difluoromethyl, trifluoromethyl, trichloromethyl, 2-fluoroethyl, 2-chloroethyl, 2-bromoethyl, 1,1,1-trifluoroethyl, heptafluoropropyl, 4-chlorobutyl, 5-fluoropentyl, 6-chlorohexyl, cyanomethyl, 2-cyanoethyl, 3-cyanopropyl, 2-cyanobutyl, 4-cyanobutyl, 5-cyanopentyl, 6-cyanohexyl, 2-methoxyethyl, 2-ethoxyethyl, 2-propoxyethyl, 2-isopropoxyethyl, 2-butoxyethyl, 2-methoxypropyl, 2-ethoxypropyl, 3-ethoxypropyl, 4-ethoxybutyl, 4-isopropoxybutyl, 5-ethoxypentyl, 6-methoxyhexyl, benzyl, 1-phenylethyl, 2-phenylethyl, 4-chlorobenzyl, 4-methoxybenzyl, 2-(4-methylphenyl)ethyl, methoxycarbonylmethyl, ethoxycarbonylmethyl, 2-methoxycarbonylethyl, 2-ethoxycarbonylethyl, 3-methoxycarbonylpropyl, 3-ethoxycarbonylpropyl, 4-methoxycarbonylbutyl, 4-ethoxycarbonylbutyl, 5-methoxycarbonylpentyl, 5-ethoxycarbonylpentyl, 6-methoxycarbonylhexyl or 6-ethoxycarbonylhexyl.

Preference is given to azulenesquaric acid dyes of the formula I where $R^2$, $R^3$, $R^4$ and $R^5$ are each $C_1$–$C_6$-alkyl or hydrogen.

Preference is further given to azulenesquaric acid dyes of the formula I where $R^1$ is $C_1$–$C_{12}$-alkyl or $C_2$–$C_{12}$-alkenyl.

Particular preference is given to azulenesquaric acid dyes of the formula I in which $R^3$ and $R^4$ are each methyl, $R^3$ and $R^5$ are each hydrogen, and L and $R^1$ are each as defined above. These dyes conform to the formula Ia

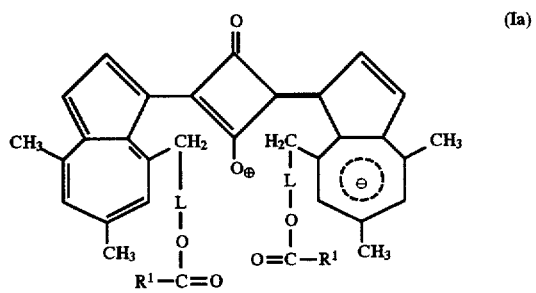

(Ia)

Very particular preference is given to azulenesquaric acid dyes of the formula I where $R^2$ and $R^4$ are each hydrogen, $R^3$ is isopropyl, $R^5$ is methyl, and L and $R^1$ are each as defined above. These dyes conform to the formula Ib

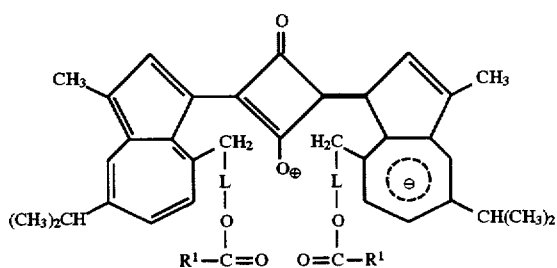

(Ib)

Preference is further given to azulenesquaric acid dyes of the formula I where $R^1$ is $C_1-C_{12}$-alkyl or $C_2-C_{12}$-alkenyl.

The dyes of the formula I are obtainable for example from azulene derivatives of the formula I, where L, $R^1$, $R^2$, $R^3$, $R^4$ and $R^5$ are each as defined above by reaction with squaric acid of the formula III according to the following equation:

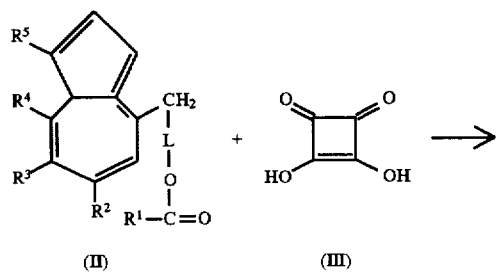

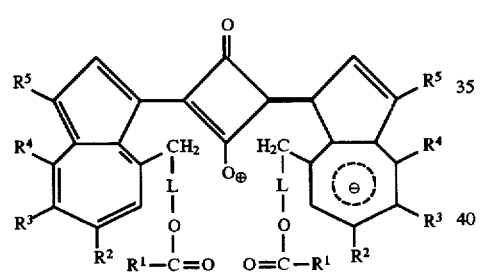

(I)

In those azulene derivatives of the formula II where $R^5$ is hydrogen, the bond to the squaric acid can form at different positions on the five-membered ring, which may produce isomeric products in which the ring positions of substituents $CH_1$—L—O—CO—$R^1$ and $R^4$ are interchanged with each other, as mentioned above. This is because it is then necessary to distinguish those compounds where the bond to the squaric acid forms on that side where the substituent $CH_3$—L—O—CO—$R^1$ is attached from those in which the bond to the squaric acid forms at that side where the substituent $R^5$ is attached. These isomeric compounds can be separated by chromatography. For use in storage layers, however, it is customary to use the isomeric mixtures.

The method of preparation is known per se and is described for example in Angew. Chem. 78 (1966), 937, and in EP-A-310,080.

The present invention further provides novel carbonyloxy-substituted azulenes of the formula II

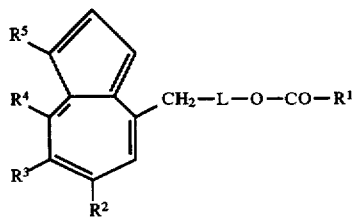

(II)

where

L is $C_1-C_{12}$-alkylene which may be substituted by phenyl, $R^1$ is $C_1-C_{12}$-alkyl, monounsaturated or polyunsaturated $C_2-C_{12}$-alkenyl, which may be phenyl-substituted, $C_2-C_2$-cycloalkyl, $C_3-C_7$-cycloalkenyl, substituted or unsubstituted phenyl, pyrrolyl, furanyl, thienyl or pyridyl and $R^2$, $R^3$, $R^4$ and $R^5$ are identical or different and each is independently of the others hydrogen or $C_1-C_{12}$-alkyl which may be substituted by halogen, $C_1-C_{12}$-alkoxy, phenyl, substituted phenyl, $C_1-C_{12}$-alkoxycarbonyl or by cyano.

Concerning examples of L, $R^1$, $R^2$, $R^3$, $R^4$ and $R^5$, reference is made to the previous lists.

The carbonyloxy-substituted azulene derivatives of the formula II are obtained by starting from the corresponding hydroalkylazulene derivatives of the formula IV

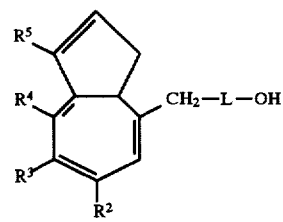

(IV)

where L, $R^2$, $R^3$, $R^4$ and $R^5$ are each as defined above. The preparation of these products is described for example in EP-A-310,080.

For instance, those azulene derivatives of the formula IVa or IVb

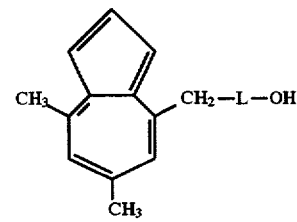

(IVa)

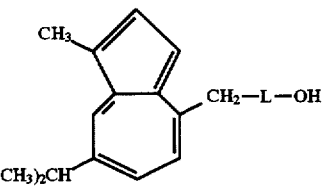

(IVb)

where L is in each case as defined above, are particularly highly suitable for conversion.

The conversion of the hydroxyalkylene derivatives IV can be effected for example with organic carboxylic acids or carbonyl halides of the formula V $R^1$—CO—X  (V)

where $R^1$ is as defined above and X is hydroxyl or halogen, in a conventional manner. To this end, the hydroxyalkylazulene IV can be reacted for example with a carbonyl chloride V (X=chlorine) in an inert organic solvent (e.g. methylene chloride, 1,1,2-trichloroethane, toluene, naphtha or tetrahydrofuran) at from 0° to 80° C. in the presence or absence of a base (for example a tertiary amine or pyridine). The hydroxyalkylazulene IV can also be converted with a carboxylic acid V (X=hydroxyl) in the presence of a condensing agent, e.g. dicyclohexylcarbodiimide, and in the presence or absence of a catalyst (e.g. dimethylaminopyridine) under the aforementioned conditions.

It is a further object of the present invention to provide a novel optical recording medium containing azulenesquaric acid derivatives as storage materials which is simple to manufacture, is easy to write to and subsequently also to read back from, for which the signal-to-noise ratio should be very high, and which exhibits high storage layer stability.

We have found that this further object is achieved by an optical recording medium comprising a base material and a radiation-sensitive thin coating film which contains a dye with or without a binder, wherein the dye has the formula I

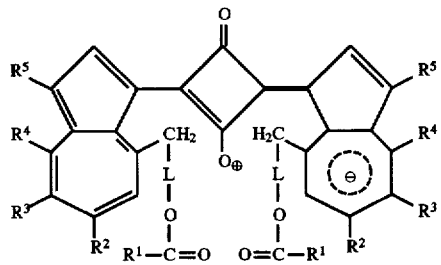

where

L is $C_1$–$C_{12}$-alkylene which may be substituted by phenyl, $R^1$ is $C_1$–$C_{12}$-alkyl, monounsaturated or polyunsaturated $C_2$–$C_{12}$-alkenyl, which may be phenyl-substituted, $C_3$–$C_7$-cycloalkyl, $C_3$–$C_7$-cycloalkenyl, substituted or unsubstituted phenyl, pyrrolyl, furanyl, thienyl or pyridyl and $R^2$, $R^3$, $R^4$ and $R^5$ are identical or different and each is independently of the others hydrogen or $C_1$–$C_{12}$-alkyl which may be substituted by halogen, $C_1$–$C_{12}$-alkoxy, phenyl, substituted phenyl, $C_1$–$C_{12}$-alkoxycarbonyl or by cyano, with the proviso that when $R^5$ is hydrogen the positions of the substituents $CH_2$—L—O—CO—$R^1$ and $R^4$ on either or both azulene rings may also be interchanged with each other within an azulene ring.

Preference is given to an optical recording medium which contains azulenesquaric acid dyes of the formula I where $R^2$, $R^3$, $R^4$ and $R^5$ are each $C_1$–$C_6$-alkyl or hydrogen.

Further preference is given to an optical recording medium containing azulenesquaric acid dyes of the formula I where $R^1$ is $C_1$–$C_{12}$-alkyl or $C_1$–$C_{12}$-alkenyl.

Particular preference is given to an optical recording medium which contains azulenesquaric acid dyes of the formula I where $R^2$ and $R^4$ are each methyl and $R^3$ and $R^5$ are each hydrogen.

Very particular preference is given to an optical recording medium which contains azulenesquaric acid dyes of the formula I where $R^2$ and $R^4$ are each hydrogen, $R^3$ is ispopropyl and $R^5$ is methyl.

Suitable base materials are conveniently transparent base materials such as glass or plastics. Suitable plastics are for example poly(meth)acrylates, polycarbonates, polyesters, epoxies, polyolefins (e.g. polymethylpentene), polyamide, polyvinyl chloride, polystyrene and polyvinyl esters.

A particularly preferred recording medium is based on a support of polycarbonate or poly(meth)acrylate, in particular polycarbonate.

Preference is further given to an optical recording medium which contains from 1 to 30% by weight, based on dye, of binder.

The novel azulenesquaric acid dyes of the formula I have good optical characteristics. In addition, the novel compounds have been observed to give very stable pure dye layers. This is because no recrystallisation of the pure dye layer was observed and it is thus possible to dispense with the addition of polymeric binders. Moreover, the lightfastness (stability) is significantly higher than that of existing methine dyes, so that the addition of stabilizers to the layer formulation can be limited to a minimum. Another particular advantage is the ready solubility of the novel dyes I in most organic solvents, so that these dyes can be applied directly (without protective layer) to structured plastics substrates, in particular polycarbonate substrates, by spincoating.

As mentioned above, the spincoating solution preferably contains a binder to ensure good long term stability and in particular to optimize its viscosity. Preferably the solution contains from 1 to 30% by weight, based on the amount of dissolved solids in the solution, of a binder.

Suitable binders are for example polyorganosiloxanes, epoxides, poly(meth)acrylates, polystyrene homopolymers and copolymers, polyvinylcarbazole, polyvinylpyrrolidone, polyimidazole copolymers, polyvinyl ester copolymers, polyvinyl ether copolymers, polyvinylidene chloride polymers, acrylonitrile copolymers, polyvinyl chloride or copolymers thereof, cellulose acetate and nitrocellulose.

A preferred recording medium contains a binder based on a vinylpyrrolidone/vinyl acetate copolymer or a polyvinyl chloride/polyvinyl ether copolymer.

The optical recording medium according to the present invention is advantageously prepared by spincoating with a solution containing an organic solvent and an azulenesquaric acid dye I, with or without a binder. Advantageously, the level of dissolved solids in the spincoating solution is from 1 to 30% by weight, based on the solution.

Suitable solvents are for example propanol, isopropanol, butanol, diacetone alcohol, methyl ethyl ketone, toluene, bromoform, 1,1,2-trichloroethane and mixtures thereof.

Optionally, the solution may also contain up to 10% by weight, based on the level of dissolved solids in the spincoating solution, of additives, for example antioxidants, singlet oxygen quenchers or UV absorbers.

Preferably, the spincoating solution contains up to 5% by weight, based on the level of dissolved solids in the spincoating solution, of a mixture of a plurality of antioxidants, singlet oxygen quenchers and UV absorbers. When using antioxidants which likewise absorb in the near infrared, for example nickel thiolene complexes, as described for example in DE-A-3,505,750, DE-A-3,505,751 or Dyes and Pigments 8 (1987), 381–88, it is preferable for up to 10% by weight, based on the level of dissolved solids in the spincoating solution, to be present in the solution.

Spincoating is for the purposes of the present invention the application of the solution to a rotating base material, which advantageously has a round shape. However, it is also possible to apply the solution to a base which is initially at rest and then set in rotation. The solution is conveniently applied to the base by means of a syringe or capillary or by means of a mechanical pump.

The base generally rotates at a speed of from 5 to 7000 rpm, preferably from 500 to 5000 rpm, the solution being advantageously applied at a relatively low speed (about 500–2000 rpm) and then dried at a higher speed (about 5000–7000 rpm). The thickness of the layer which is sensitive to laser light is from 40 to 160 nm, preferably from 80 to 120 nm. The thickness is dependent on the speed of rotation, the concentration and viscosity of the spincoating solution and the temperature.

In the optical recording medium according to the present invention, the layer which is sensitive to laser light is present in the form of a homogeneous, thin, smooth layer of high optical quality. For instance, the reflectivities are in general within a range greater than 12%.

The novel recording medium is also sufficiently sensitive to the wavelength of the laser light source used; that is, the incidence of light pulses having an energy content of a few nJ which are focused to a focal spot diameter of $\leq 1$ µm leads to the formation of pits with an excellent signal-to-noise ratio.

Particularly suitable laser light sources on account of the small size of the device, its low energy consumption and the possibility of direct modulation of the optical output through modulation of the electrical drive current are solid state injection lasers which emit in the near infrared, in particular the AlGaAs laser which emits within the wavelength range from about 750 to 900 nm.

The Examples which follow further illustrate the invention.

EXAMPLE 1
Preparation of 3-(7-isopropyl-1-methylazulen-4-yl)butyl acetate 4.8 g (0.063 mol) of acetyl chloride in 20 ml of dichloromethane were added dropwise at 0° C. to a solution of 12.1 g (0.05 mol) of 3-(7-isopropyl-1-methylazulen-4-yl)butanol and 7.9 g (0.1 mol) of pyridine in 100 ml of dichloromethane, and the mixture was stirred at room temperature for 1 hour. It was then extracted with 30 ml of 2N hydrochloric acid, and the organic phase was washed neutral and dried over sodium sulfate. The residue remaining behind after evaporating off the solvent was chromatographed (silica gel; 9:1 v/v petroleum ether/ethyl acetate). This gave 12.6 g (89%) of the acetate as a highly viscous blue oil.

Physical data: IR (KBr): 2959, 2929 (CH); 1741 (C=O); 1555, 1463, 1436, 1387, 1365, 1241, 1047 cm$^{-1}$. $^1$H-NMR (CDCl$_2$): δ=1.38 (d, 6H); 2.05 (s, 3H); 2.16 (cm, 2H); 2.68 (s, 3H); 3.08 (cm, 1H); 2.22 (cm, 2H); 4.18 (cm, 2H); 6.95 (d, 1H); 7.30 (d, 1H); 7.40 (d, 1H); 7.64 (d, 1H); 8.18 (s, 1H) ppm. $^{13}$C-NMR (CDCl$_3$): δ=1286; 20.85; 24.72 (2C); 30.17; 34.53; 38.28; 64.22; 112.19; 124.41; 125.46; 133.30; 135.13; 136.39; 136.59; 137.28; 140.04; 147.55; 170.90 ppm. MS: m/e=284.4 (C$_{19}$H$_{24}$O$_2$$^+$, 50%).

The method of Example 1 was used to prepare the carboxylic esters listed in Table 1, which were characterized by IR, $^1$H-NMR, $^{13}$C-NMR and MS spectra and also by GC.

If hydroxyalkylazulenes are reacted with crotonic or sorbic acid derivatives in the presence of stronger bases, e.g. triethylamine, then, in contradistinction to the above method, a partial or complete isomerization of the double bond takes place (see Example 2).

EXAMPLE 2
Preparation of 3-(7-isobutyl-1-methylazulen-4-yl)butyl 3-butenecarboxylate 10.0 g (0.07 mol) of crotonyl chloride were added dropwise at room temperature to a solution of 7.26 g (0.03 mol) of 3-(7-isobutyl-1-methylazulen-4-yl)butanol and 30 ml of triethylamine in 100 ml of tetrahydrofuran, and the mixture was stirred for 2 hours. 50 ml of water were then added, and the batch was thoroughly stirred. It was then extracted with methyl t-butyl ether, the extract was dried over sodium sulfate, the solvent was evaporated off, and the residue remaining behind was chromatographed over silica gel (9:1 v/v petroleum ether/ethyl acetate). This gave 8.2 g (88%) of a product, which was uniform according to GC, as a highly viscous blue oil. Physical data: IR (KBr): 2959, 2927 (CH); 1738 (C=O); 1464, 1423, 1388, 1327, 1256, 1173, 921 cm$^{-1}$. $^1$H-NMR (CDCl$_3$): δ=1.47 (d, 6H); 2.18 (cm, 2H); 2.65 (s, 3H); 3.08 (m, 3H); 3.20 (t, 2H); 4.18 (t, 2H); 5.18 (m, 2H); 5.94 (m, 1H); 6.95 (d, 1H); 7.28 (bs, 1H); 7.40 (d, 1H); 7.62 (bs, 1H); 8.18 (s, 1H) ppm. $^{13}$C-NMR (CDCl$_3$): δ=12.84; 24.71 (2C); 30.18; 34.50; 38.28; 39.23; 64.41; 112.33; 118.36; 124.39; 125.47; 130.49; 133.28; 135.10; 136.42; 136.60; 137.31; 140.04; 147.49; 171.29 ppm. MS: m/e=310.4 (C$_{21}$H$_{28}$O$_2$$^+$, 80%)

TABLE 1

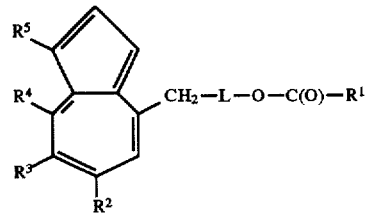

| Example No. | —L—O—C(O)R$^1$ | R$^2$ | R$^3$ | R$^4$ | R$^5$ | MS[M$^P$] | IR (CO) [cm$^{-1}$] |
|---|---|---|---|---|---|---|---|
| 3 | —CH$_2$—CH$_2$—O—C(O)CH | H | C(CH$_3$)$_2$ H | H | CH$_3$ | C$_{19}$H$_{24}$O$_2$ 284.4 | 1741 |
| 4 | —CH—CH$_2$—O—C(O)CH$_3$<br>  \|<br>  C$_2$H$_5$ | H | C(CH$_3$)$_2$ H | H | CH$_3$ | C$_{21}$H$_{28}$O$_2$ 284.4 | 1741 |
| 5 | —CH$_2$—CH$_2$—O—C(O)-t-Bu | H | C(CH$_3$)$_2$ H | H | CH$_3$ | C$_{22}$H$_{30}$O$_2$ 326.4 | 1728 |
| 6 | —CH$_2$—CH$_2$—O—C(O)—(CH$_2$)$_3$—CH$_3$ | H | C(CH$_3$)$_2$ H | H | CH$_3$ | C$_{22}$H$_{30}$O$_2$ 326.5 | 1736 |

TABLE 1-continued

| Example No. | —L—O—C(O)R¹ | R² | R³ | R⁴ | R⁵ | MS[M^D] | IR (CO) [cm⁻¹] |
|---|---|---|---|---|---|---|---|
| 7 | —CH—CH₂—O—C(O)—(CH₂)₃—CH₃<br>\|<br>C₂H₅ | H | C(CH₃)₂<br>H | H | CH₃ | C₂₄H₃₄O₂<br>354.5 | 1736 |
| 8 | —CH₂—CH₂—O—C(O)—(CH₂)₈—CH₃ | H | C(CH₃)₂<br>H | H | CH₃ | C₂₇H₄₀O₂<br>396.6 | 1734 |
| 9 | —CH₂—CH₂—O—C(O)—CH=CH₂ | H | C(CH₃)₂<br>H | H | CH₃ | C₂₀H₂₄O₂<br>296.4 | 1724 |
| 10 | —CH—CH₂—O—C(O)—CH=CH₂<br>\|<br>C₂H₅ | H | C(CH₃)₂<br>H | H | CH₃ | C₂₂H₂₈O₂<br>324.5 | 1726 |
| 11 | CH₃<br>\|<br>—CH₂—CH₂—O—C(O)—C=CH₂ | H | C(CH₃)₂<br>H | H | CH₃ | C₂₁H₂₆O₂<br>310.4 | 1718 |
| 12 | CH₃<br>\|<br>—CH—CH₂—O—C(O)—C=CH₂<br>\|<br>C₂H₅ | H | C(CH₃)₂<br>H | H | CH₃ | C₂₃H₃₀O₂<br>338.5 | 1719 |
| 13 | —CH₂—CH₂—O—C(O)—CH=CH—CH₃ | H | C(CH₃)₂<br>H | H | CH₃ | C₂₁H₂₆O₂<br>310.4 | 1720 |
| 14 | —CH—CH₂—O—C(O)—CH=CH—CH₃<br>\|<br>C₂H₅ | H | C(CH₃)₂<br>H | H | CH₃ | C₂₃H₃₀O₂<br>338.5 | 1721 |
| 15 | —CH₂—CH₂—O—C(O)—CH=CH—CH=CH—CH₃ | H | C(CH₃)₂<br>H | H | CH₃ | C₂₃H₂₈O₂<br>336.5 | 1713 |
| 16 | —CH—CH—CH₂—O—C(O)—CH=CH—CH=CH—CH₃<br>\|<br>C₂H₅ | H | C(CH₃)₂<br>H | H | CH₃ | C₂₅H₃₂O₂<br>364.5 | 1713 |
| 17 |  | H | C(CH₃)₂<br>H | H | CH₃ | C₂₆H₂₈O₂<br>372.5 | 1712 |
| 18 | 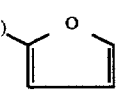 | H | C(CH₃)₂<br>H | H | CH₃ | C₂₈H₃₂O₂<br>400.6 | 1712 |
| 19 | 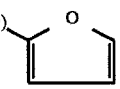 | H | C(CH₃)₂<br>H | H | CH₃ | C₂₂H₂₄O₃<br>336.4 | 1728 |
| 20 | 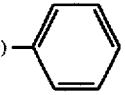 | H | C(CH₃)₂<br>H | H | CH₃ | C₂₄H₂₈O₃<br>364.5 | 1727 |
| 21 | —CH₂—CH₂—O—C(O)—C₆H₅ | H | C(CH₃)₂<br>H | H | CH₃ | C₂₄H₂₆O₂<br>346.5 | 1718 |
| 22 | 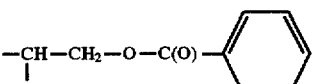 | H | C(CH₃)₂<br>H | H | CH₃ | C₂₆H₃₀O₂<br>374.5 | 1718 |

TABLE 1-continued

[Structure: azulene core with R5, R4, R3, R2 substituents and CH2—L—O—C(O)—R1 group]

| Example No. | —L—O—C(O)R¹ | R² | R³ | R⁴ | R⁵ | MS[M⁰] | IR (CO) [cm⁻¹] |
|---|---|---|---|---|---|---|---|
| 23 | —CH₂—CH(C₂H₅)—O—C(O)—(3,4,5-tri-OMe-phenyl) | H | C(CH₃)₂H | H | CH₃ | C₂₆H₃₀O₂ 374.5 | 1715 |

EXAMPLE 25

Preparation of the bis[3-(7-isobutyl-1-methylazulen-4-yl) butyl acetate]squaric acid dye A mixture of 15.9 g (0.056 mol) of 3-(7-isobutyl-1-methylazulen-4-yl)butyl acetate, 5.0 g of squaric acid and 80 ml of 1:1 toluene/butanol was refluxed for 2 hours under a water separator. After the solvent had been distilled off, the residue was recrystallized from ethyl acetate. This gave 3.0 g (17%) of the dye as metallically shiny, pale brown crystals of melting point 180°–181° C. Physical data: IR (KBr): 2985 (CH); 1736, 1612 (C=O); 1437, 1386, 1337, 1323, 1252, 1243, 1020 cm⁻¹. UV (CH₂Cl₂): $\lambda_{max}(\epsilon)$=766 (116000) nm.

$^1$H-NMR (CDCl₃): δ=1.38 (d, 12H); 1.89 (s, 6H); 1.95 (m, 4H); 2.55 (s, 6H); 3.08 (cm, 2H); 3.95 (m, 8H); 7.48 (d, 2H); 7.60 (d, 2H); 8.12 (s, 2H); 8.88 (s, 2H) ppm. $^{13}$C-NMR (CDCl₃): δ=12.96 (2C); 20.73 (4C); 24.21 (2C); 30.53 (2C); 36.17 (2C); 38.33 (2C); 63.66 (2C); 121.58 (2C); 130.87 (2C); 133.97 (2C); 134.38 (2C); 138.18 (2C); 139.82 (2C); 141.84 (2C); 147.49 (2C); 150.31 (2C); 155.54 (2C); 170.75 (2C); 181.79 (2C); 183.07 (2C) ppm. MS: m/e 646.8 (C₄₂H₄₄O₈, 50%).

The method of Example 24 was used to prepare the squaric acid dyes listed in Table 2, which were additionally characterized by IR, $^1$H-NMR, $^{13}$C-NMR and MS spectra.

TABLE 2

(I)

[Structure: bis-azulenyl squaric acid dye with R², R³, R⁴, R⁵ substituents and L—O—C(O)—R¹ groups on both azulene units]

| Example No. | —L—O—C(O)R¹ | R² | R³ | R⁴ | R⁵ | $\lambda_{max}$ (ε) CH₂Cl₂ | m.p. [°C.] |
|---|---|---|---|---|---|---|---|
| 25 | —CH(C₂H₅)—CH₂—O—C(O)CH₃ | H | C(CH₃)₂H | H | CH₃ | 768 (108000) | 167–167 |
| 26 | —CH₂—CH₂—O—C(O)-t(Bu) | H | C(CH₃)₂H | H | CH₃ | 768 (102000) | 189 |
| 27 | —CH₂—CH₂—O—C(O)—(CH₂)₃—CH₃ | H | C(CH₃)₂H | H | CH₃ | 768 (113000) | 181–182 |
| 28 | —CH(C₂H₅)—CH₂—O—C(O)—(CH₂)₃—CH₃ | H | C(CH₃)₂H | H | CH₃ | 768 (1113000) | 163–164 |
| 29 | —CH₂—CH₂—O—C(O)—(CH₂)₈—CH₃ | H | C(CH₃)₂H | H | CH₃ | 765 (111000) | 70–72 |

TABLE 2-continued (I)

| Example No. | −L−O−C(O)R¹ | R² | R³ | R⁴ | R⁵ | $\lambda_{max}$ (g) $CH_2Cl_2$ | m.p. [°C.] |
|---|---|---|---|---|---|---|---|
| 30 | −CH₂−CH₂−O−C(O)−CH=CH₂ | H | C(CH₃)₂ H | H | CH₃ | 769 (112000) | 115–116 |
| 31 | −CH(C₂H₅)−CH₂−O−C(O)−CH=CH₂ | H | C(CH₃)₂ H | H | CH₃ | 772 (107000) | 99–101 |
| 32 | −CH₂−CH₂−O−C(O)−C(CH₃)=CH₂ | H | C(CH₃)₂ H | H | CH₃ | 770 (117000) | 135–136 |
| 33 | −CH(C₂H₅)−CH₂−O−C(O)−C(CH₃)=CH₂ | H | C(CH₃)₂ H | H | CH₃ | 773 (111000) | 171–172 |
| 34 | −CH₂−CH₂−O−C(O)−CH=CH−CH₃ | H | C(CH₃)₂ H | H | CH₃ | 770 (114000) | 183–184 |
| 35 | −CH(C₂H₅)−CH₂−O−C(O)−CH=CH−CH₃ | H | C(CH₃)₂ H | H | CH₃ | 772 (106000) | 103–105 |
| 36 | −CH₂−CH₂−O−C(O)−CH₂−CH=CH₂ | H | C(CH₃)₂ H | H | CH₃ | 770 (118000) | 97–98 |
| 37 | −CH₂−CH₂−O−C(O)−CH=CH−CH=CH−CH₃ | H | C(CH₃)₂ H | H | CH₃ | 770 (115000) | 129–130 |
| 38 | −CH(C₂H₅)−CH₂−O−C(O)−CH=CH−CH=CH−CH₃ | H | C(CH₃)₂ H | H | CH₃ | 772 (114000) | 213–214 |
| 39 | −CH₂−CH₂−O−C(O)−C=CH−C₆H₅ | H | C(CH₃)₂ H | H | CH₃ | 768 (117000) | 172–173 |
| 40 | −CH(C₂H₅)−CH₂−O−C(O)−CH=CH−C₆H₅ | H | C(CH₃)₂ H | H | CH₃ | 772 (118000) | 180–181 |
| 41 | −CH₂−CH₂−O−C(O)−(furyl) | H | C(CH₃)₂ H | H | CH₃ | 766 (118000) | 200–201 |
| 42 | −CH(C₂H₅)−CH₂−O−C(O)−(furyl) | H | C(CH₃)₂ H | H | CH₃ | 770 (108000) | 163–164 |
| 43 | −CH₂−CH₂−O−C(O)−C₆H₅ | H | C(CH₃)₂ H | H | CH₃ | 768 (123000) | 230–231 |
| 44 | −CH(C₂H₅)−CH₂−O−C(O)−C₆H₅ | H | C(CH₃)₂ H | H | CH₃ | 771 (120000) | 207 |

TABLE 2-continued

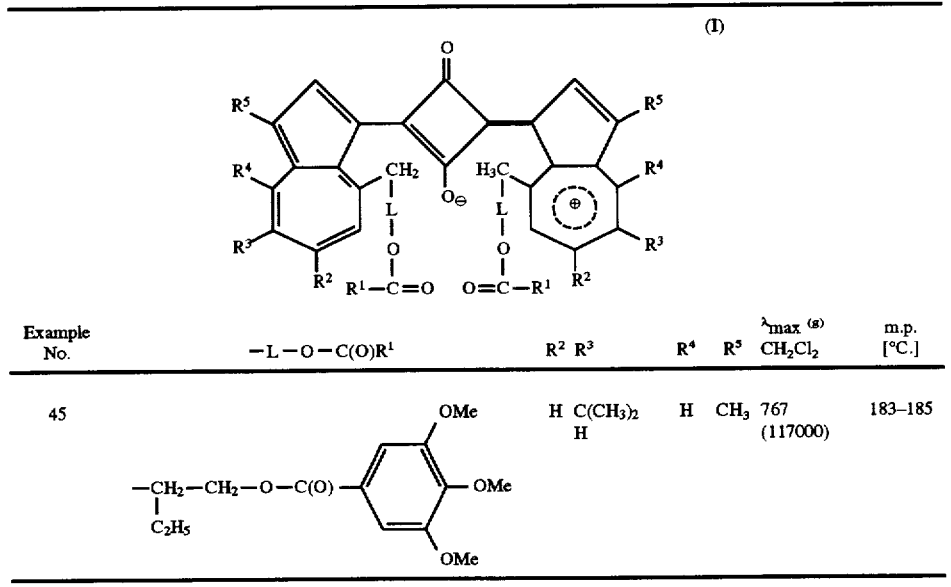

| Example No. | —L—O—C(O)R¹ | R² R³ | R⁴ R⁵ | $\lambda_{max}$ (s) $CH_2Cl_2$ | m.p. [°C.] |
|---|---|---|---|---|---|
| 45 | -CH₂-CH₂-O-C(O)-[3,4,5-triOMe-phenyl], with C₂H₅ branch | H C(CH₃)₂ H | H CH₃ | 767 (117000) | 183–185 |

EXAMPLE 46

An approximately 5% strength by weight solution of the dye of Example 24 in 1:1 v/v propanol/diacetone alcohol was applied with a syringe to a polymethyl methacrylate disk rotating at about 2000 rpm, and the remaining solvent was then spun off at 5000 rpm. This produced a homogenous, highly reflective dye layer which was very readily writable with a semiconductor laser (λ=830 nm). The data can be read back with very good contrast.

EXAMPLE 47

A 3% strength by weight solution of the dye of Example 24 in 1:1 v/v propanol/diacetone alcohol which contained 30% by weight, based on the level of dissolved solids in the solution, of polymethyl methacrylate was applied to a grooved polycarbonate disk by spincoating as described in Example 46. This produced a homogeneous, highly reflective dye layer which is firmly adherent to the substrate, gives a good image of the grooves on the substrate and is very readily writable with a semiconductor laser (λ=830 nm). The written data were stable under hot moist conditions and can be read back with good contrast as often as desired.

EXAMPLE 48

A 2% strength by weight solution of the dye of Example 24 in 1:1 v/v propanol/diacetone alcohol which, based on the level of dissolved solids in the solution, contained 10% by weight of phenolic resin as binder and 5% by weight of 4-octyl-4'-fluorodiphenyldithiolenenickel as stabilizer was applied to a grooved polycarbonate disk by spincoating as described in Example 46. The storage layer obtained is similar in all respects to that of Example 47, but is more stable to UV light.

EXAMPLE 49

A 2% strength by weight solution of the dye of Example 24 in toluene which, based on the level of dissolved solids in the solution, contained 10% by weight of polymethyl methacrylate and 5% by weight of biscampheratodithiolenenickel was applied to a glass disk by spincoating as described in Example 46. The resulting dye layer was homogeneous and showed a high background reflectivity. It was readily writable with a semiconductor laser (λ=780 nm). The written data are stable under the usual test conditions and can be read back as often as desired.

We claim:

1. A carbonyloxy-substituted azulenesquaric acid dye of the formula I

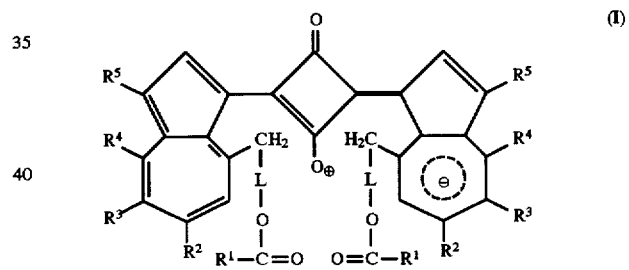

where
L is $C_1$–$C_{12}$-alkylene which may be substituted by phenyl,
R is monounsaturated or polyunsaturated $C_1$–$C_{12}$-alkenyl, which may be phenyl-substituted, $C_5$–$C_7$-cycloalkenyl, pyrrolyl, furanyl, thienyl or pyridyl and
$R^2$, $R^3$, $R^4$ and $R^5$ are identical or different and each is independently of the others hydrogen or $C_1$–$C_{12}$-alkyl, which may be substituted by halogen, $C_1$–$C_{12}$-alkoxy, phenyl, substituted phenyl, $C_1$–$C_{12}$-alkoxycarbonyl or by cyano,
with the proviso that when $R^5$ is hydrogen the positions of the substituents $CH_2$—L—O—CO—$R^1$ and $R^4$ on either or both azulene rings may also be interchanged with each other within an azulene ring.

2. An azulenesquaric acid dye as claimed in claim 1, wherein $R^2$, $R^3$, $R^4$ and $R^5$ are each $C_1$–$C_8$-alkyl or hydrogen.

3. An azulenesquaric acid dye as claimed in claim 1, wherein $R^2$ and $R^4$ are each methyl and $R^3$ and $R^5$ are each hydrogen.

4. An azulenesquaric acid dye as claimed in claim 1, wherein $R^2$ and $R^4$ are each hydrogen, $R^3$ is isopropyl and $R^5$ is methyl.

* * * * *